United States Patent
Herzenberg et al.

(12)

(10) Patent No.: US 6,566,401 B2
(45) Date of Patent: May 20, 2003

(54) N-ACETYLCYSTEINE COMPOSITIONS AND METHODS FOR THE TREATMENT AND PREVENTION OF DRUG TOXICITY

(75) Inventors: Leonard A. Herzenberg, Stanford, CA (US); Leonore A. Herzenberg, Stanford, CA (US); Stephen C. De Rosa, Bethesda, MD (US); James Andrus, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/833,228

(22) Filed: Apr. 11, 2001

(65) Prior Publication Data

US 2002/0142991 A1 Oct. 3, 2002

Related U.S. Application Data

(60) Provisional application No. 60/280,600, filed on Mar. 30, 2001.

(51) Int. Cl.$^7$ .......................................... A61K 31/195
(52) U.S. Cl. ..................................................... 514/562
(58) Field of Search ........................................ 514/562

(56) References Cited

U.S. PATENT DOCUMENTS 4,757,063 A  7/1988  Parnham .................... 514/183
5,474,757 A * 12/1995  Yang .......................... 514/562

OTHER PUBLICATIONS

Macrides et al, 125CA:212153, 1996.*
Donovan, Medical Fortune–telling: Predicting Acetaminophen Toxicity, Academic Emergency Medicine, vol. 6, No. 11, pp. 1079–1082 (Nov. 1999).
Chassaing, et al. Determination of Reduced and Oxidized Homocysteine and Related Thiols in Plasma by Thiol–Specific Pre–Column Derivatization and Capillary Electrophoresis with Laser–Induced Fluorescence Detection, J. Chromatography B, 735, pp. 219–227 (1999).
Bond, et a., Population–based Incidence and Outcome of Acetaminophen Poisoning by Type of Ingestion, Academic Emergency Medicine, vol. 6, No. 11, pp. 1115–1120 (Nov. 1999).
Garcia de la Asuncion, et al., AZT Treatment Induces Molecular and Ultrastructural Oxidative Damage to Muscle Mitochondria, J. Clin. Invest., vol. 102, No. 1, pp. 4–9 (Jul. 1998).
Gogu, et al., Protection of Zidovudine–induced Toxicity Against Murine Erythroid Progenitor Cells by Vitamin E, Exp. Hematol., vol. 19, pp. 649–652 (1991).
Gogu, et al., The Protective Role of Zinc and N–Acetylcysteine in Modulating Zidovudine Induced Hematopoietic Toxicity, Life Sciences, vol. 59, No. 15, pp. 1323–1329 (1996).
Prakash, et al., The Human Immunodeficiency Virus Type 1 Tat Protein Potentiates Zidovudine–Induced Cellular Toxicity in Transgenic Mice, Archives of Biochemistry and Biophysics, vol. 343, No. 2, pp. 173–180 (Jul. 15, 1997).
Richman, et al., The Toxicity of Azidothymidine (AZT) in the Treatment of Patients with AIDS and AIDS–Related Complex, The New England Journal of Medicine, vol. 317, No. 4, pp. 192–197 (Jul. 23, 1987).
Choi, et al., Molecular Mechanism of Decreased Glutathione Content in Human Immunodeficiency Virus Type 1 Tat–trangenic Mice, J. Biological Chemistry, vol. 275, No. 5, pp. 3693–3698 (Feb. 4, 2000).
Thomas, Paracetamol (Acetaminophen) Poisoning, Pharmac. Ther., vol. 60, pp. 91–120 (1993).
Sarnstrand, et al., N,N'–Diacetyl–L–cystine—The Disulfide Dimer of N–acetylcysteine—Is a Potent Modulator of Contact Sensitivity/Delayed Type Hypersensitivity Reactions in Rodents, J. Pharmacology and Experimental Therapeutics, vol. 288, No. 3, pp. 1174–1184 (1999).

* cited by examiner

*Primary Examiner*—Russell Travers
(74) *Attorney, Agent, or Firm*—Greenberg Traurig, LLP; Eugene C. Rzucidlo; Beverly W. Lubit

(57) ABSTRACT

The invention provides pharmaceutical compositions for the treatment or prevention of the toxic effects of therapeutic agents and methods of treating or preventing such toxicity using a toxicity reducing amount of N-acetylcysteine either alone or in combination with a therapeutically effective amount or, to achieve its therapeutic advantages, an amount larger than what is customarily given as a therapeutically effective amount, of a therapeutic agent. The invention also provides pharmaceutical compositions for the treatment or prevention of the toxic effects of therapeutic agents and methods of treating or preventing such toxicity using a toxicity reducing amount of N-acetylcysteine either alone or in combination with a therapeutically effective amount or, to achieve its therapeutic advantages, an amount larger than what is customarily given as a therapeutically effective amount, of a therapeutic agent whose side effects are made worse by increased oxidative stress or treatment related decreases in subject cysteine/glutathione levels or are otherwise relieved by administration of NAC.

2 Claims, No Drawings

US 6,566,401 B2

N-ACETYLCYSTEINE COMPOSITIONS AND METHODS FOR THE TREATMENT AND PREVENTION OF DRUG TOXICITY

CROSS-REFERENCE TO RELATED APPLICATIONS

This application claims priority from U.S. Patent Application No. 60/280,600, filed Mar. 30, 2001 the contents of which are incorporated by reference herein.

GOVERNMENT SUPPORT

This work is supported at least in part by grants from the N.I.H. CA42509-14. The government may have certain rights in this invention.

FIELD OF THE INVENTION

The present invention relates to compositions for the treatment or prevention of drug toxicity in mammals including humans which may result from the administration of therapeutic agents and to methods of treating or preventing such toxicity. The compositions of this invention comprise a toxicity-reducing amount of N-acetylcysteine (NAC) alone or in combination with a therapeutically effective amount or, to achieve its therapeutic advantages, an amount larger than what is customarily given as a therapeutically effective amount, of a therapeutic agent, preferably in combination with a pharmaceutically acceptable carrier. The method of treating or preventing drug toxicity in humans comprises administering a toxicity-reducing amount of NAC alone or in combination with a therapeutically effective amount or, to achieve its therapeutic advantages, an amount larger than what is customarily given as a therapeutically effective amount, of a therapeutic agent, preferably in combination with a pharmaceutically acceptable carrier.

BACKGROUND OF THE INVENTION

Glutathione (GSH), a tripeptide that is normally found in all animal cells and most plants and bacteria at relatively high (1–10 millimolar) concentrations, helps to protect cells against oxidative damage that would otherwise be caused by free radicals and reactive oxidative intermediates (ROIs) produced during cell metabolism or as the results of, for example, drug overdose. Glutathione is itself the major scavenger of reactive oxidative intermediates present in all eukaryotic forms of life and is generally required to protect cells against damage by oxidants. Glutathione reduces (and thereby detoxifies) intracellular oxidants and is consumed by this reaction. Glutathione is oxidized to the disulfide linked dimer (GSSG), which is actively pumped out of cells and becomes largely unavailable for reconversion to reduced glutathione. Thus, unless glutathione is resynthesized through other pathways, utilization of this compound is associated with a reduction in the amount of glutathione available. The antioxidant effects of glutathione are also mediated less directly by the role of this compound in maintaining other antioxidants in reduced form. Thus, pharmaceutical compounds that replenish or elevate glutathione levels work, at least in part, through enhancement of the defense mechanisms seemingly utilized to normally protect tissue from ROI mediated damage.

Glutathione depletion has been implicated in the pathology of a number of diseases including infection by human immunodeficiency virus (HIV). In HIV infection, cysteine/glutathione depletion is known to impair T-cell function and is associated with impaired survival of subjects with less than 200 CD4 T-cells per $\mu l$ blood.

Drug toxicity is a very widespread problem. Cysteine/glutathione depletion and oxidative stress (See U.S. Pat. No. 4,757,063) intensify drug toxicity effects and have been implicated in the mechanism of drug toxicity reactions.

For example, acetaminophen is known to act to deplete cysteine/glutathione and cause a variety of drug toxicity symptoms. Acetaminophen, also known as paracetamol and N-acetyl-p-aminophenol, is one of the most widely used pharmaceutical analgesic and antipyretic agents in the world. It is contained in over 100 products and is commonly found in the U.S. as immediate release tablets and as extended-release preparations. Various children's chewable, suspension, and elixir formulations that contain acetaminophen are prevalent. Acetaminophen is also found as a component of combination drugs, such as propoxyphene/acetaminophen and oxycodone/acetaminophen.

Acetaminophen continues to be the most commonly encountered substance in toxic ingestions. In many cases, acetaminophen overdoses are unintentional and are undiagnosed until after substantial damage has already occurred. Repeated administration of acceptable size doses of acetaminophen can produce toxicity symptoms. As discussed by Donovan (1999) *Academic Emergency Med.* 6:1079–1082, methods for detecting post-ingestion blood levels of acetaminophen suffer from poor predictive values. Even in the simple case of a single acute ingestion, patients with no discernible risk factors for liver injury and low blood levels of acetaminophen still develop toxicity and even die.

Many companies package acetaminophen under different trade names, resulting in inadvertent overdosing by less sophisticated patients and parents who do not read the information on the packaging. In addition, cold remedies and other over-the-counter preparations often contain acetaminophen, which is listed among a series of generic drug names that are difficult for patients and parents to read. Therefore, patients often are unaware of the amount of acetaminophen that they have received. Children are especially vulnerable to accidental exposure due to their smaller size, the presence of acetaminophen in multiple over-the-counter remedies, and a reluctance to administer aspirin and other NSAIDs to children for fever due to the risk of Reye's Syndrome and renal tubular injury. The antipyretic value of acetaminophen clearly has been demonstrated and hence acetaminophen is widely used in hospitals for this purpose. However, acetaminophen may not be the antipyretic agent of choice under circumstances where renal or hepatic function is in danger of being compromised.

It is well established that large acetaminophen overdose causes hepatotoxicity and, in some cases, nephrotoxicity in humans and in experimental animals. Acute overdosage of acetaminophen results in dose-dependent and potentially fatal hepatic necrosis as well as (in rare cases) renal tubular necrosis and hypoglycemia. Acetaminophen is rapidly absorbed from the stomach and small intestine and is normally metabolized by conjugation in the liver to nontoxic agents, which are then eliminated in the urine. In acute overdoses, or when maximum daily doses are exceeded over a prolonged period, the normal pathways of metabolism become saturated.

Excess acetaminophen is metabolized in the liver via the mixed function oxidase P450 system to a toxic, N-acetyl-p-benzoquinone-Imine (NAPQI). NAPQI has an extremely short half-life and is rapidly conjugated with glutathione, a sulfhydryl donor, and removed from the system. Under conditions of excessive NAPQI formation or reduced glutathione stores, NAPQI is free to bind to vital proteins and the lipid bilayer of hepatocytes. This results in hepatocellular death and subsequent centrilobular liver necrosis. Immumunohistochemical studies have suggested that NAPQI-protein adducts appear even at sub-hepatotoxic acetaminophen doses and before depletion of total hepatic glutathione which may be related to rare cases of hypersensitivity. In addition, decreased intracellular cysteine/glutathione can contribute to cell death via mechanisms that do not involve NAPQI.

The direct cost of acetaminophen overdose has been estimated to be $87 million annually. Effective protocols have been developed and tested to stratify risk and treat patients who present soon after a single large dose of acetaminophen. However, many patients present after a delay long enough to metabolize all the acetaminophen, after two or more ingestions over several hours, or after several days of excessive self-medication. Under these circumstances it is difficult for the clinician to estimate the risk of adverse outcome before hepatic or renal injury occurs. See, for example, Bond and Hite (1999) *Acad. Emerg. Med.* 6:1115–1120; and Donovan (1999) *Acad. Emerg. Med.* 6:1079–1082. However, early treatment of acetaminophen overdosage is considered to be crucial, and vigorous supportive therapy is essential when intoxication is severe.

Nucleoside reverse transcriptase inhibitors (NRTIs), of which the pyrimidine nucleoside analogue azidothymidine (AZT, zidovudine), is a common example, are often given in combination therapies with other anti-retroviral drugs to treat HIV. Long-term therapy with AZT is commonly associated with dose-dependent hematologic toxicity which manifests as low erythrocyte counts and elevated mean red cell volume, and with muscle fiber toxicity, particularly in patients with advanced HIV disease. Some studies indicate that AZT's toxic interactions result from the generation of reactive oxygen species (ROIs) that react with and deplete intracellular glutathione levels. See de la Asuncion, et al (1998) *J. Clin. Invest.* 102(1): 4–9; Gogu et al. (1991) *Exp. Hematol.* 19(7): 649–652; Gogu and Agrawal (1996) *Life Sci.* 59 (16): 1323–1329; Prakash et al (1997) *Arch. Biochem. Biophys.* 343 (2): 173–80.

Results have shown that acetaminophen usage, which lowers glutathione levels exacerbates AZT toxicity. Richman, et al. (1987) *N. Eng. J. Med.* 317: 192–97. De Rosa et al. recently have shown that treatment with NAC which increases glutathione levels decreases the toxicity. De Rosa et al., submitted to JAMA for publication.

Evidence from in vitro and animal studies supports this conclusion. AZT treatment caused oxidative damage to mitochondrial DNA (including increased mitochondrial lipoperoxidation) and increased levels of oxidized glutathione in skeletal muscle in mice. See de la Asuncion, et al. (1998) *J. Clin. Invest.* 102(1): 4–9. NAC and the antioxidant Vitamins C and E have been shown to prevent this AZT-induced toxicity. See id.; Gogu, et al (1991) *Exp. Hematol.* 19, 649–52; and Gogu and Agrawal (1996) *Life Chem. Rep.* 4, 1–35. Furthermore, AZT treatment intensifies glutathione depletion in HIV-TAT transgenic mice (see Prakash, O., et al. *Arch. Biochem. Biophys.* (1997) 343: 173–80) where expression of the TAT protein has been shown to deplete glutathione by decreasing glutathione biosynthesis (see Choi, J., et al., (2000) *J. Biol. Chem.* 275 (5): 3693–98) and the activity of antioxidant enzymes (Flores et al. (1993) *Proc. Nat. Acad. Sci.* 90 (16): 7632–36). Studies with TAT-transgenic mice also show that AZT toxicity is enhanced in this glutathione-depleted environment. See Prakash et al. (1997) *Arch. Biochem. Biophys.* 343, 173–80.

Early clinical trials of AZT efficacy in HIV disease revealed an association between AZT toxicity and the use of acetaminophen. See, e.g., Richman, et al. (1987) *New Eng. J. Med.* 317(4): 192–97. Although the mechanism of this toxic reaction is not fully understood, acetaminophen does not impair AZT detoxification since no difference in AZT's rate of destruction has been observed. Since acetaminophen is known to deplete glutathione, the potentially harmful effect of co-administering acetaminophen and AZT appears to be mediated through glutathione depletion. Thus, in conditions where glutathione already is depleted, such as in later stages of HIV disease, detoxification of acetaminophen (which can be expected to further deplete glutathione stores in the liver and elsewhere) would increase the potential for AZT toxicity.

Long-term antibiotic usage also often produces drug toxicity reactions. Toxicity reactions for a given antibiotic are a function of its mechanism of action and the pathway(s) by which it is metabolically degraded.

Scientists have long sought to identify agents that will be generally effective in combating drug toxicity reactions. Protective agents for drug overdose have been extensively studied. A known method of treatment for acetaminophen overdose is the administration of sulfhydryl compounds. L-methionine, L-cysteine, and either the purified L-enantiomer or the racemate mixture of N-acetylcysteine are known to have a protective action in animals. Methionine and another sulfhydryl compound, cysteamine, have been reported to provide some protection. Also, cimetidine, dimethyl sulfoxide, and ethanol have been shown to inhibit acetaminophen bioactivation. N-acetylcysteine has been shown to be effective in humans when given orally. Early administration of compounds supplying sulfhydryl groups (0 to 10 hours after acetaminophen ingestion) may prevent or minimize hepatic and renal injury in cases of acetaminophen overdose. NAC is now used by many physicians for treatment of hepatic failure of any etiology, whether known or unknown, and is the accepted antidote for cyclophosphamide poisoning. NAC also is used to prevent toxicity due to radiation therapy contrast material in patients undergoing such treatment. The mechanisms through which NAC prevents or reverses toxicity are mainly thought to involve glutathione replenishment. However, additional mechanisms through which NAC works directly via the cysteine molecule itself are not excluded.

Recently we have shown that treatment with NAC decreases AZT's hematologic toxicity in subjects taking AZT. It appears that NAC provides cysteine needed to redress the excessive sulfur loss that occurs in HIV disease and specifically to replenish intracellular glutathione. This in turn helps to restore the reducing power necessary for deoxynucleotide synthesis and to bring the size of the deoxynucleotide pool, and hence the rate of cell division, back into normal range. This decreases the AZT-mediated inhibition of erythroid development, helps to improve the overall metabolism and stability of erythrocytes and their progenitors (for example, by enabling optimal functioning of the glucose-6-phosphate dehydrogenase and other energy-supplying pathways). In addition, it improves the cell's ability to withstand the production of oxidants induced by the introduction of drugs (such as AZT) and the internal production of molecules (such as TNF and HIV-TAT) that trigger intracellular oxidant production.

Improved formulations and methods to prevent drug toxicity reactions during long term therapy are of particular interest in view of the considerable loss of life attributable to, and cost of treatment of, such reactions. The present invention addresses this problem.

SUMMARY OF THE INVENTION

Pharmaceutical compositions and methods of treatment are provided for serial or co-administration of NAC with any therapeutic agent to decrease drug toxicity, including those drugs whose side effects are made worse by decreases in subject intracellular cysteine/gluathione levels or increased oxidative stress, or whose side effects are otherwise relieved by administration of NAC. The serial or co-administration of NAC makes a therapeutic agent safer at currently recognized standard therapeutic doses and allows increased doses of that therapeutic agent to be administered for its beneficial purposes without toxic side effects.

According to one embodiment of the invention, compositions useful for treating or preventing the toxic effects of therapeutic agents in mammals are provided comprising a toxicity-reducing amount of N-acetylcysteine or a pharmaceutically acceptable salt or derivative thereof alone or in combination with a therapeutic or greater amount of a therapeutic agent, in combination with a pharmaceutically acceptable excipient or carrier. In another embodiment, such compositions comprise at least about 1 mg N-acetylcysteine or a pharmaceutically-acceptable salt or derivative thereof. In another embodiment, such compositions comprise a therapeutic amount of a therapeutic agent in combination with a toxicity-reducing amount of NAC or a pharmaceutically acceptable salt or derivative thereof, wherein the therapeutic agent is at least one antibiotic or antiviral agent. In another embodiment, such compositions comprise a therapeutic amount of a therapeutic agent in combination with a toxicity-reducing amount of NAC or a pharmaceutically acceptable salt or derivative thereof, wherein the therapeutic agent is at least one antibiotic or antiviral agent that produces oxidative stress. In another embodiment, such compositions comprise a therapeutic amount of a therapeutic agent in combination with a toxicity-reducing amount of NAC or a pharmaceutically acceptable salt or derivative thereof, wherein the therapeutic agent is at least one antibiotic or antiviral agent that produces treatment-related decreases in subject cysteine/glutathione levels. In another embodiment, such compositions comprise a therapeutic amount of a therapeutic agent in combination with a toxicity-reducing amount of NAC or a pharmaceutically acceptable salt or derivative thereof, wherein the therapeutic agent is an analgesic, antipyretic or other therapeutic compound. In another embodiment, such compositions comprise a therapeutic amount of a therapeutic agent in combination with a toxicity-reducing amount of NAC or a pharmaceutically acceptable salt or derivative thereof, wherein the therapeutic agent is an analgesic, antipyretic or other therapeutic compound that produces oxidative stress. In another embodiment, such compositions comprise a therapeutic amount of a therapeutic agent in combination with a toxicity-reducing amount of NAC or a pharmaceutically acceptable salt or derivative thereof, wherein the therapeutic agent is an analgesic, antipyretic or other therapeutic compound that produces treatment-related decreases in subject cysteine/glutathione levels. In another embodiment, such compositions comprise a therapeutic amount of a therapeutic agent in combination with a toxicity-reducing amount of NAC or a pharmaceutically acceptable salt or derivative thereof, wherein the compound is a paraminophenol derivative, which includes phenacetin and its active metabolite acetaminophen. In another embodiment, such compositions comprise a therapeutic amount of a therapeutic agent in combination with a toxicity-reducing amount of NAC or a pharmaceutically acceptable salt or derivative thereof, wherein each dosage unit contains a standard dose of acetaminophen and at least about 1 mg of NAC. In another embodiment, such compositions comprise a therapeutic amount of a therapeutic agent in combination with a toxicity-reducing amount of NAC or a pharmaceutically acceptable salt or derivative thereof, wherein the therapeutic agent is an anti-retroviral agent. In another embodiment, such compositions comprise a therapeutically effective amount of AZT in combination with a toxicity-reducing amount of NAC to decrease key aspects of AZT toxicity in human HIV patients, e.g., macrocytic anemia.

In another embodiment, a method of treating or preventing the toxic effects of therapeutic agents in mammals comprises administering a toxicity reducing amount of NAC or a pharmaceutically acceptable salt or derivative thereof, alone or in combination with a normal dosage or a greater than normal dosage of a therapeutic agent, in combination with a pharmaceutically acceptable carrier. In another embodiment, the method comprises administering at least about 1 mg NAC or a pharmaceutically acceptable salt or derivative thereof to a patient receiving nutrition parenterally. In another embodiment, the method comprises administering a therapeutic amount of at least one antibiotic or antiviral agent in combination with NAC or a pharmaceutically acceptable salt or derivative thereof. In another embodiment, the method comprises administering a therapeutic amount of at least one antibiotic or antiviral agent in combination with NAC or a pharmaceutically acceptable salt or derivative thereof wherein the antibiotic or antiviral agent produces oxidative stress. In another embodiment, the method comprises administering a therapeutic amount of at least one antibiotic or antiviral agent in combination with a toxicity-reducing amount of NAC or a pharmaceutically acceptable salt or derivative thereof, wherein the antibiotic or antiviral agent produces treatment-related decreases in subject cysteine/glutathione levels. In another embodiment, the method comprises administering a therapeutic amount of an anti-retroviral agent in combination with a toxicity reducing amount of NAC. In another embodiment, the method comprises administering a therapeutic amount of an anti-retroviral agent in combination with a toxicity-reducing amount of NAC wherein the anti-retroviral agent is AZT. In another embodiment, the method comprises administering a therapeutic amount of AZT serially or in combination with a toxicity-reducing amount of NAC perinatally. In another embodiment, the method comprises administering a therapeutic amount of AZT serially or in combination with a toxicity-reducing amount of NAC neonatally. In another embodiment, the method comprises administering a therapeutic amount of AZT for suspected or known exposure to the HIV virus serially or in combination with a toxicity-reducing amount of NAC. In another embodiment, the method comprises administering a therapeutic amount of at least one analgesic, antipyretic or other therapeutic compound in combination with a toxicity reducing amount of NAC or a pharmaceutically acceptable salt or derivative thereof. In another embodiment, the method comprises administering a therapeutic amount of at least one analgesic, antipyretic or other therapeutic compound in combination with a toxicity-reducing amount of NAC, wherein the compound produces oxidative stress. In another embodiment, the method comprises administering a therapeutic amount of at least one analgesic, antipyretic or other therapeutic compound in combination with a toxicity-reducing amount of NAC, wherein the compound produces treatment-related decreases in subject cysteine/glutathione levels. In another embodiment, the method comprises administering a therapeutic amount of at least one analgesic, antipyretic or other therapeutic compound in combination with a toxicity-reducing amount of NAC wherein the compound is a paraminophenol derivative, which includes phenacetin and its active metabolite acetaminophen. In another embodiment, the method comprises administering a therapeutic amount of acetaminophen in a standard dosage serially or in combination with at least about 1 mg per dose N-acetylcysteine to treat a fever or pain in a patient who responds normally to acetaminophen. In another embodiment, the method comprises administering a greater than standard dosage of acetaminophen serially or in combination with at least about 4 mg/kg N-acetylcysteine to treat a fever nonresponsive to the standard dose of acetaminophen. In another embodiment, the method comprises administering a standard dosage of acetaminophen serially or in combination with at least about 1 mg per dose N-acetylcysteine to treat patients who require acetaminophen during their exposure to radiation contrast agents.

The combined compositions and methods provide protection against toxic drug reactions, particularly where overdosing may be inadvertent, undiagnosable, or even therapeutically desirable if the toxic side effects could be removed.

DETAILED DESCRIPTION OF THE INVENTION

The invention described herein provides for the serial or co-administration of any therapeutically active agent with NAC to relieve the toxic effects of such therapy in mammals including where toxic effects of such therapy in mammals may be due to oxidative stress or treatment-related decreases in subject cysteine/glutathione levels or are otherwise relieved by administration of NAC.

The pharmaceutical compositions and methods of treatment above described include providing the pharmaceutical compositions in oral, parenteral or suppository form for oral, parenteral or rectal administration. It is preferred that the NAC be substantially free of sulfones or other chemicals that interfere with the metabolism of the co-administered drug, e.g., acetaminophen, in its bioactive form. It is also preferred that the NAC be substantially free of its oxidized form, di-n-acetylcysteine. It is preferred that the therapeutic agent, serially or co-administered, be in any form in which it is typically available and the composition should be prepared in a manner that substantially prevents oxidation of the NAC during preparation or storage.

In one aspect of the invention, the combined formulation is administered to individuals having an increased susceptibility for acetaminophen toxicity. With regard to acetaminophen toxicity in adults, hepatotoxicity may occur after ingestion of a single dose of more than about 7.5 to 10 g of acetaminophen. However, alcoholics and individuals taking isoniazid have elevated P-450 2E1 levels and can have increased susceptibility for acetaminophen toxicity. The risk of hepatotoxicity with single or serial doses of acetaminophen may also be increased in patients regularly taking other hepatic enzyme-inducing agents, especially barbiturates or other anticonvulsants. In addition, individuals taking classes of antibiotics that reduce GSH, including sulfas, chloramphenicol, macrolides and fluoroquinolones, may have increased risk of hepatotoxicity with acetaminophen. Also, although most acetaminophen is metabolized through the glucoronidation pathway in adults, some is converted to a reactive intermediate that is detoxified in a GSH-dependent reaction. See Thomas, S. H. (1993) *Pharmacol. Ther.* 60: 91–120. Pre-adolescent children, particularly below school age, lack the normal glucoronidation pathway and rely to a greater degree than adults on GSH for detoxification of acetaminophen, increasing their susceptibility to acetaminophen-induced-toxicity. Further, patients receiving parenteral nutrition who may not receive an adequate dietary source of cysteine or whose condition may result in oxidative stress will have an increased susceptibility to acetaminophen toxicity. Increased susceptibility can also result from a predisposition to GSH deficiency, due to HIV and other infections, metabolic diseases, e.g., diabetes, chronic diseases, sepsis, hepatic insufficiency and other physiologic oxidative stress.

With respect to acetaminophen, the formulations of the present invention find use as anti-pyretic and analgesic agents, and are suitable for medical indications treatable with acetaminophen alone. An improvement in product safety is provided by the inclusion of NAC, which substantially prevents the possibility of accidental or inadvertent overdosage. The combined use of acetaminophen and NAC enhances the desired effects of acetaminophen while preventing its side effects, e.g. administering acetaminophen with NAC can allow acetaminophen dosing at higher levels, which would otherwise carry an unacceptable risk of toxicity. The co-formulation with NAC can enhance the safety of acetaminophen administration in severe illness and hence decrease patient morbidity and mortality due to acetaminophen-induced hepatic and renal injury. NAC administration may provide an additional benefit since it tends to reduce the negative effects of tumor necrosis factor alpha (TNF-α) and similar-acting cytokines.

NAC replenishes glutathione following acetaminophen overdose, which otherwise leads to a fatal depletion of glutathione in the liver. This non-toxic drug enters cells readily and replenishes the intracellular cysteine required to produce glutathione, thus leading to an increase in glutathione levels. It is important to note that NAC does not interfere with the peripheral action of acetaminophen as an analgesic or anti-pyretic, and thus its presence in the combined formulations of the invention does not decrease the potency of the therapeutic agent. It may be noted that the effectiveness of NAC depends on the presence of the reduced form, which may, for example, liberate the reduced form of glutathione from homo- and hetero-disulfide derivatives in thiol-disulfide exchange reactions. The unit dose of acetaminophen in the provided formulation may be higher than the conventional dose in the absence of NAC. A typical unit dosage may be a solution suitable for oral or intravenous administration; an effervescent tablet suitable for dissolving in water, fruit juice, or carbonated beverage and administered orally; a tablet taken from two to six times daily, or one time-release capsule or tablet taken once or twice a day and containing a proportionally higher content of active ingredient, etc. The time-release effect may be obtained by capsule materials that dissolve at different pH values, by capsules that release slowly by osmotic pressure, or by any other known means of controlled release. Unit dosage forms may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the unit dosage forms of the present invention depend on the effect to be achieved and the intended recipient.

It is preferred that the pharmaceutical compositions according to the present invention contained from about 80 mg to about 2000 mg of acetaminophen per dosage unit, particularly from about 650 mg to about 2000 mg per dosage unit. The amount of NAC per dosage unit is preferably from 1 mg to 25000 mg, preferably at least 3 mg to 2,000 mg per dosage unit for oral administration, and 20–20,000 mg for parenteral.

The acetaminophen present in orally administrable solid unit doses will usually be at least about 80 mg (for pediatric doses), 325 mg, 500 mg and 650 mg, and may be as high as about 2000 mg, more usually not more than about 1500 mg together with effective amounts of NAC. Suppositories are formulated in the manner well known in the art and usually comprise at least about 120 mg, 125 mg, 325 mg, 500 mg and 650 mg acetaminophen per dosage unit and may be as high as about 2000 mg, more usually not more than about 1500 mg together with effective amounts of NAC. Oral liquid dosage forms usually comprise at least about 100 mg/ml, 120 mg/2.5 ml, 120mg/5 ml, 160 mg/5 ml, 165 mg/5 ml, 325 mg/5 ml acetaminophen, and may be as high as about 2000 mg, more usually not more than about 1500 mg together with effective amounts of NAC.

The unit dose of NAC, in combination with any one of the above doses of acetaminophen, or alone for the treatment of acute hepatic injury in the absence of toxic levels of acetaminophen, will usually comprise at least about 1.5 mg/kg to a maximum amount of 70 mg/kg (for pediatric doses), usually at least about 500 mg (for adult doses); and usually not more than about 2,000 mg at the physician's discretion. Patients on therapy known to deplete cysteine/ glutathione or produce oxidative stress may benefit from higher amounts of NAC.

Over-the-counter NAC can be variably produced and packaged. Because the production and packaging methods generally do not guard against oxidation, the NAC can be significantly contaminated with bioactive oxidation products. These may be particularly important in view of data indicating that the oxidized form of NAC has effects counter to those reported for NAC and is bioactive at doses roughly 10–100 fold less than NAC (see Samstrand et al (1999) *J. Pharmacol. Exp. Ther.* 288: 1174–84).

The distribution of the oxidation states of NAC as a thiol and disulfide depends on the oxidation/reduction potential. The half-cell potential obtained for the NAC thiol/disulfide pair is about +63 mV, indicative of its strong reducing activity among natural compounds (see Noszal et al. (2000) *J. Med. Chem.* 43:2176–2182). In a preferred embodiment of the invention, the preparation and storage of the formulation is performed in such a way that the reduced form of NAC is the primary form administered to the patient. Maintaining NAC containing formulations in solid form is preferable for this purpose. When in solution, NAC containing formulations are preferably stored in a brown bottle that is vacuum sealed. Storage in cool dark environments is also preferred.

The determination of reduced and oxidized species present in a sample may be determined by various methods known in the art, for example with capillary electrophoresis, HPLC, etc. as described by Chassaing et al. (1999) *J Chromatogr B Biomed Sci Appl* 735(2):219–27.

The compositions of the present invention may be administered orally, parenterally, or rectally in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques. Topical administration may also involve the use of transdermal administration such as transdermal patches or iontophoresis devices which are prepared according to techniques and procedures well known in the art.

Solid dosage forms for oral administration may include capsules, tablets, pills, powders, granules and gels. In such solid dosage forms, the active compounds may be admixed with at least one inert diluent such as sucrose, lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Suppositories for rectal administration of the drug composition, such as for treating pediatric fever etc., can be prepared by mixing the drug with a suitable nonirritating excipient such as cocoa butter and polyethylene glycols which are solid at ordinary temperatures but liquid at the rectal temperature and will therefore melt in the rectum and release the drug.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1, 3-butanediol. Among the acceptable vehicles and solvents that may be employed are water, Ringer's solution, and isotonic sodium chloride solution. In addition, sterile, fixed oils are conventionally employed as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/ or dextran. Optionally, the suspension may also contain stabilizers.

The composition, if desired, can also contain minor amounts of wetting or emulsifying agents or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

The therapeutically active agent of the present invention can be formulated per se or in salt form. Pharmaceutically acceptable salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of compounds in the compositions of the present invention which will be effective in the treatment of a particular disorder or condition will depend on the nature of the disorder or condition, and can be determined by standard clinical techniques. See, for example, Goodman and Gilman; The Physician's Desk Reference, Medical Economics Company, Inc., Oradell, N.J., 1995; and to Drug Facts and Comparisons, Facts and Comparisons, Inc., St. Louis, Mo., 1993. As the addition of NAC does not affect the therapeutic efficacy of acetaminophen, it is generally not necessary to adjust the dosage from what would ordinarily be administered for acetaminophen alone, and in fact the dose may be raised due to the increased safety of the present formulations. The precise dose to be employed in the formulation will also depend on the route of administration, and the seriousness of the disease or disorder, and should be decided according to the judgment of the practitioner and each patient's circumstances.

The present invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In another embodiment of the invention, formulations of NAC are provided for the treatment of acute hepatic failure of unknown etiology, for example for the treatment of acetaminophen or other drug toxicity where the serum levels of the toxic drug indicate non-toxic levels where there may be an increased risk for toxicity due to oxidative stress or other aspects of the patient's condition. The NAC formulations for treatment of such patients will utilize a formulation as described above.

Many such patients having severe hepatic failure also have serum levels of acetaminophen within the accepted non-toxic range, due to various factors. Such factors may include the lapsed time before presentation of the toxic effects, for example in incidences of intentional overdose.

Inadvertent acetaminophen toxicity has also been reported with normally accepted dosing regimens when associated with certain viral infections, toxic exposure, and drug use, such as sulfa, chloramphenicol and erythromycin. Many of these patients present with non-toxic acetaminophen levels, but toxicity still results from oxidative stress and other drug-related effects on hepatocytes.

Another group of patients are under oxidative stress or otherwise have severe illness that makes them more susceptible than normal to acetaminophen toxicity. Such patients may include, for example, patients with septic shock, distributive shock, hemorrhagic shock, acute respiratory distress syndrome, organ failure, and closed head injury. Patients in this group are routinely treated with acetaminophen as an anti-pyretic and mild analgesic, which may inadvertently result in severe hepatic or renal damage.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. We present AZT and acetaminophen as examples of the model for toxicity we propose. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A child or adult having a fever can be treated with a formulation comprising 15 mg/kg acetaminophen and 1 mg/kg of either the purified L-enantiomer or the racemate mixture composed of equal proportions of the D- and L-isomers of NAC administered either serially or co-administered three or four times a day up to the highest tolerable dose, given that there will be individual variability in the ability to tolerate NAC. The dose of NAC may vary from 0.03 to four times the amount of acetaminophen taken.

Example 2

A child or adult having a fever that does not respond to acetaminophen at a standard dose level can be treated with a formulation comprising 15–50 mg/kg acetaminophen and 3–130 mg/kg of either the purified L-enantiomer or the racemate mixture composed of equal proportions of the D- and L-isomers of NAC administered either serially or co-administered three or four times a day up to the highest tolerable dose, given that there will be individual variability in the ability to tolerate NAC.

Example 3

A normally healthy child or adult having a low fever can be treated for several days at normal acetaminophen dosage levels with a formulation comprising 80 mg per tablet acetaminophen and 3 mg per tablet of either the purified L-enantiomer or the racemate mixture composed of equal proportions of the D- and L-isomers of NAC administered either serially or co-administered three or four times a day up to the highest tolerable dose, given that there will be individual variability in the ability to tolerate NAC, the number of tablets to vary according to the patient's circumstances and body weight.

Example 4

A child or adult receiving nutrition parenterally can be treated to supplement the nutrition formula with a formulation comprising 3 mg or more of either the purified L-enantiomer or the racemate mixture composed of equal proportions of the D- and L-isomers of NAC administered three or four times a day up to the highest tolerable dose, given that there will be individual variability in the ability to tolerate NAC, variability in the amount of the cysteine source in the total parenteral nutrition formulation and the variability of the concomitantly administered drugs.

Example 5

A child or adult having liver failure or liver damage or having elevated liver enzymes and fever who is already compromised can be treated with a cold, pain, antipyretic or other formulation comprising between 4 and 10 mg/kg acetaminophen and up to 130 mg/kg of either the purified L-enantiomer or the racemate mixture composed of equal proportions of the D- and L-isomers of NAC administered either serially or co-administered three or four times a day up to the highest tolerable dose given that there will be individual variability in the ability to tolerate NAC.

Example 6

A patient having HIV infection can be treated with a formulation comprising a therapeutically effective amount of AZT as part of a multi-drug antiviral regimen and a toxicity-reducing amount of either the purified L-enantiomer or the racemate mixture composed of equal proportions of the D- and L-isomers of NAC administered either serially or co-administered two, three or four times a day up to the highest tolerable dose, given that there will be individual variability in the ability to tolerate NAC. It is preferred that NAC be formulated at high doses as an effervescent tablet or in granular form in a single dose packet to be dissolved in water to prevent untoward stomach effects. This dosage of NAC is sufficient to decrease key aspects of AZT toxicity in human HIV patients.

Example 7

AZT and NAC can be administered perinatally and neonatally to prevent vertical transmission of the HIV virus to the child. Before delivery, the mother is treated with a therapeutically effective amount of AZT and a toxicity-reducing amount of either the purified L-enantiomer or the racemate mixture composed of equal proportions of the D- and L-isomers of NAC administered either serially or co-administered two, three, or four times a day to the highest tolerable dose, given that there will be individual variability in the ability to tolerate NAC. Dosage is continued to the child after delivery to prevent oxidative stress and other AZT toxicity. It is preferred that NAC be formulated at high doses as an effervescent tablet or in granular form in a single dose packet to be dissolved in water to prevent untoward stomach effects. This dosage of NAC is sufficient to decrease key aspects of AZT toxicity in human HIV patients.

Example 8

A patient with newly-diagnosed or suspected exposure to HIV can be treated with a formulation comprising a therapeutically effective amount of AZT or other similar anti-retroviral drug as normally used and a toxicity-reducing amount of either the purified L-enantiomer or the racemate mixture composed of equal proportions of the D- and L-isomers of NAC administered either serially or co-administered two, three or four times a day up to the highest tolerable dose, given that there will be individual variability in the ability to tolerate NAC. It is preferred that NAC be formulated at high doses as an effervescent tablet or in granular form in a single dose packet to be dissolved in water to prevent untoward stomach effects. This dosage of NAC is sufficient to decrease key aspects of AZT toxicity in human HIV patients.

While the present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition useful for treating or preventing the toxic effects of therapeutic agents in mammals, comprising a toxicity-reducing amount of N-acetylcysteine or a pharmaceutically acceptable salt or derivative thereof alone or in combination with a therapeutic or greater amount of acetaminophen or a derivative thereof, in combination with a pharmaceutically acceptable excipient or carrier, wherein a unit dose of N-acetylcysteine, in combination with acetaminophen or a derivative thereof, comprises at least about 1.5 mg/kg and not more than about 2.000 mg.

2. A pharmaceutical composition according to claim 1 wherein each dosage unit contains at least about 1 mg N-acetylcysteine or a pharmaceutically-acceptable salt or derivative thereof.

* * * * *

UNITED STATES PATENT AND TRADEMARK OFFICE
CERTIFICATE OF CORRECTION

PATENT NO. : 6,566,401 B2 Page 1 of 1
APPLICATION NO. : 09/833228
DATED : May 20, 2003
INVENTOR(S) : Leonard A. Herzenberg et al.

It is certified that error appears in the above-identified patent and that said Letters Patent is hereby corrected as shown below:

In claim 1, column 14, line 57: the period (".") within the numeral "2.000" should read as a comma (--,--)

Signed and Sealed this

Eleventh Day of November, 2008

JON W. DUDAS
*Director of the United States Patent and Trademark Office*